United States Patent
Pacaccio et al.

(10) Patent No.: US 11,045,212 B2
(45) Date of Patent: Jun. 29, 2021

(54) INSTRUMENTS FOR DRILLING HOLES FOR BONE SCREWS

(71) Applicant: Aristotech Industries GmbH, Luckenwalde (DE)

(72) Inventors: Douglas Pacaccio, Sycamore, FL (US); Jeremy Blair, Atlanta, GA (US); Emmanuel Anapliotis, Berlin (DE)

(73) Assignee: Aristotech Industries GmbH, Luckenwalde (DE)

( * ) Notice: Subject to any disclaimer, the term of this patent is extended or adjusted under 35 U.S.C. 154(b) by 17 days.

(21) Appl. No.: 16/357,867

(22) Filed: Mar. 19, 2019

(65) Prior Publication Data

US 2019/0290299 A1    Sep. 26, 2019

Related U.S. Application Data

(60) Provisional application No. 62/645,983, filed on Mar. 21, 2018.

(51) Int. Cl.
*A61B 17/17* (2006.01)
*A61B 17/16* (2006.01)
(Continued)

(52) U.S. Cl.
CPC ...... *A61B 17/1728* (2013.01); *A61B 17/1615* (2013.01); *A61B 17/1617* (2013.01); *A61B 17/1633* (2013.01); *A61B 17/8625* (2013.01); *A61B 90/06* (2016.02); *A61B 17/8061* (2013.01); *A61B 2017/0046* (2013.01); *A61B 2090/062* (2016.02)

(58) Field of Classification Search
CPC ............ A61B 17/1728; A61B 17/1615; A61B 17/1617; A61B 17/1633; A61B 17/8625; A61B 17/8061; A61B 2017/0046; A61B 90/06; A61B 2090/062
See application file for complete search history.

(56) References Cited

U.S. PATENT DOCUMENTS

| 1,479,325 A | 1/1924 | Schubnel |
| 4,341,206 A | 7/1982 | Perrett et al. |

(Continued)

FOREIGN PATENT DOCUMENTS

EP    3085321 A1    10/2016

*Primary Examiner* — Kevin T Truong
*Assistant Examiner* — Tracy L Kamikawa
(74) *Attorney, Agent, or Firm* — Andrus Intellectual Property Law, LLP

(57) ABSTRACT

An instrument for drilling a hole for a bone screw comprises a shaft having a primary drill fluted portion, a shank, and a middle portion there between. Part of an outer surface of the shaft's middle portion is non-curved. A sleeve surrounds the shaft. The sleeve has an inner surface that is complementary to the outer surface of the shaft's middle portion such that the sleeve slides with respect to the shaft. The sleeve's inner surface contacts the outer surface of the shaft's middle portion at the non-curved part such that the shaft can transmit torque to the sleeve. A countersink drill bit is provided at an end of the sleeve proximate the shaft's primary drill fluted portion. A locking mechanism selectively holds the sleeve in a fixed position with respect to the shaft, locating the countersink drill bit at a selected position with respect to the shaft's drilling end.

16 Claims, 10 Drawing Sheets

(51) Int. Cl.
*A61B 17/86* (2006.01)
*A61B 90/00* (2016.01)
A61B 17/80 (2006.01)
A61B 17/00 (2006.01)

(56) References Cited

U.S. PATENT DOCUMENTS

| | | | |
|---|---|---|---|
| 4,549,538 A | 10/1985 | Shadrack, III et al. | |
| 5,626,607 A * | 5/1997 | Malecki | A61B 17/00234 |
| | | | 606/205 |
| 5,895,389 A | 4/1999 | Schenk et al. | |
| 7,491,203 B2 * | 2/2009 | Harris, Jr. | A61B 17/1617 |
| | | | 606/80 |
| 8,795,282 B2 * | 8/2014 | Earl | A61B 17/155 |
| | | | 606/86 R |
| 8,876,444 B1 * | 11/2014 | Chanturidze | B23B 51/104 |
| | | | 408/191 |
| 9,408,742 B2 * | 8/2016 | Dineen | A61B 17/0401 |
| 9,498,229 B2 | 11/2016 | Harris, Jr. et al. | |
| 9,550,237 B2 * | 1/2017 | Keightley | B23B 31/005 |

* cited by examiner

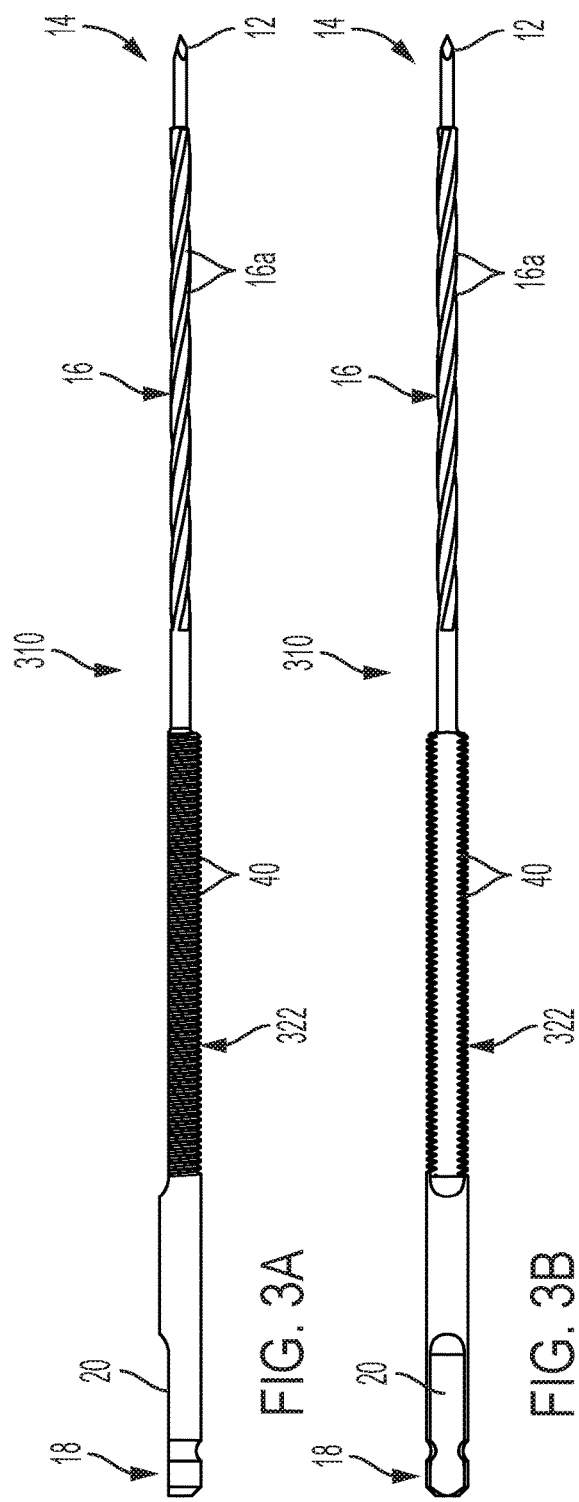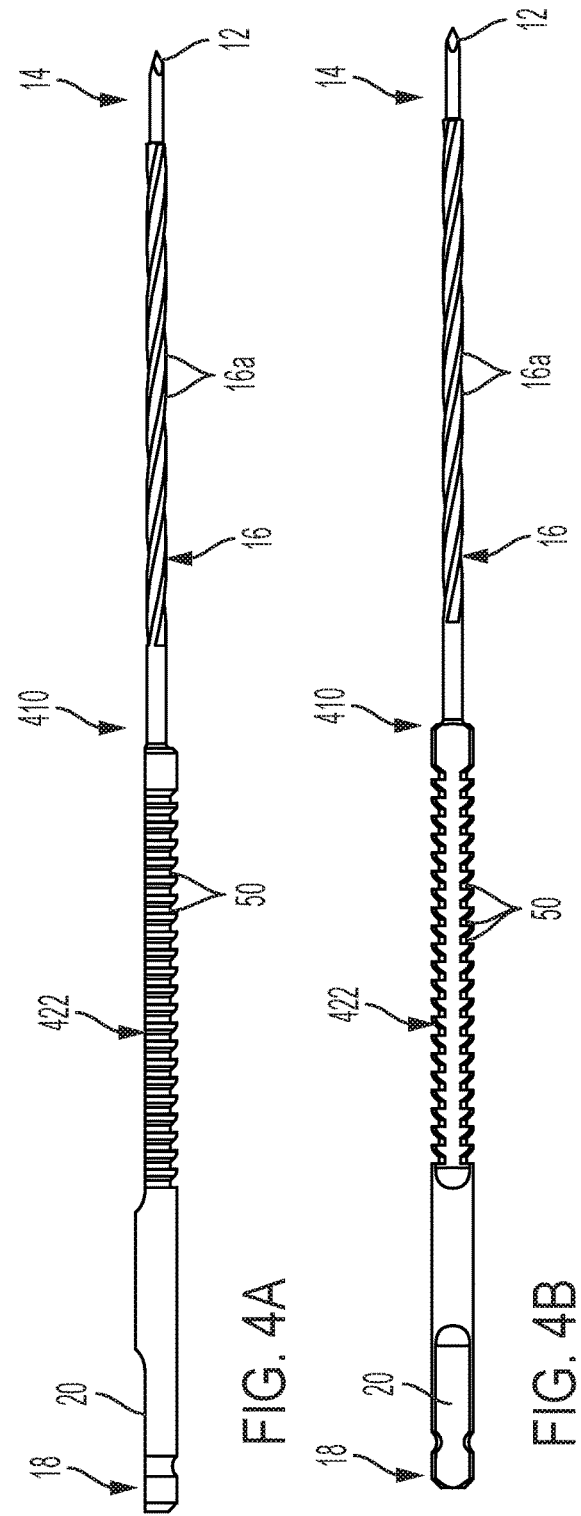

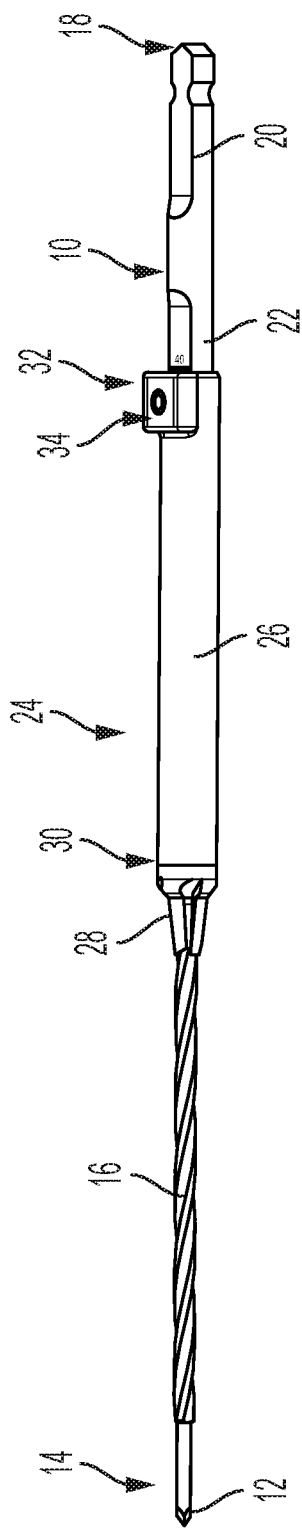
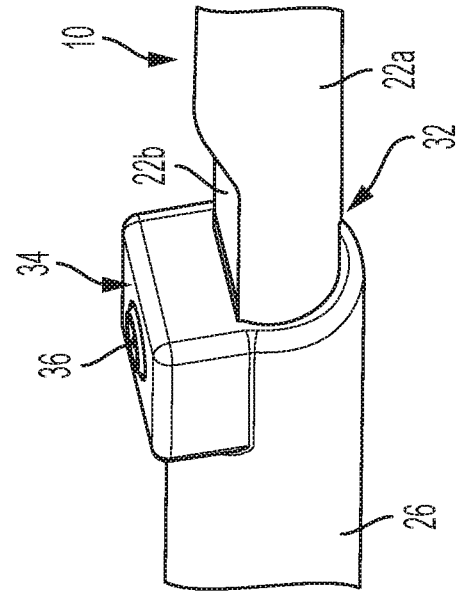
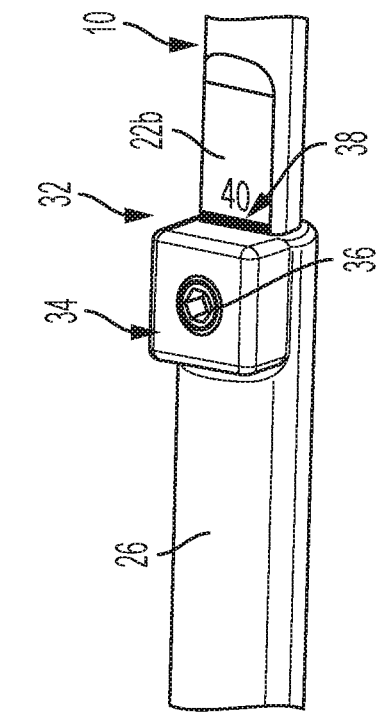
FIG. 5
FIG. 5B
FIG. 5A

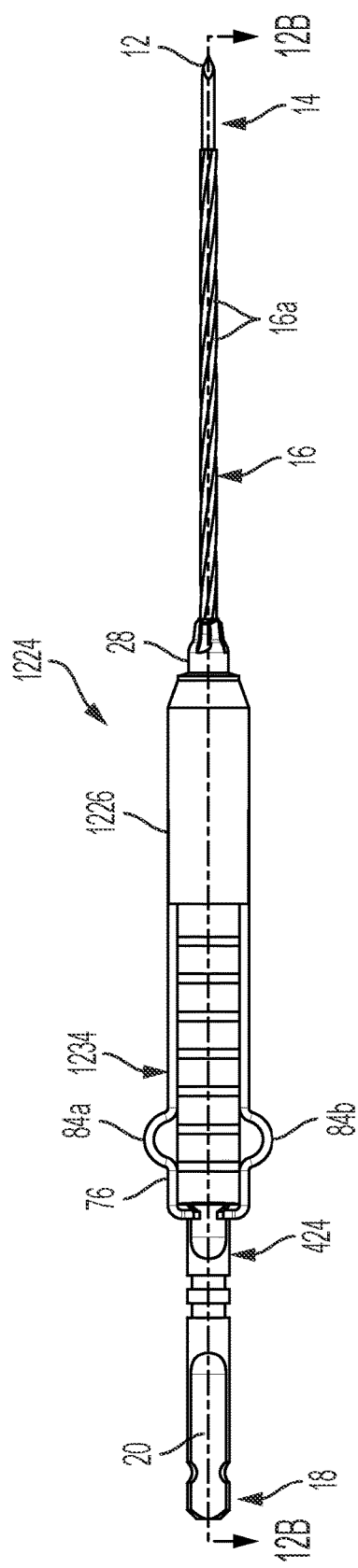
FIG. 12A
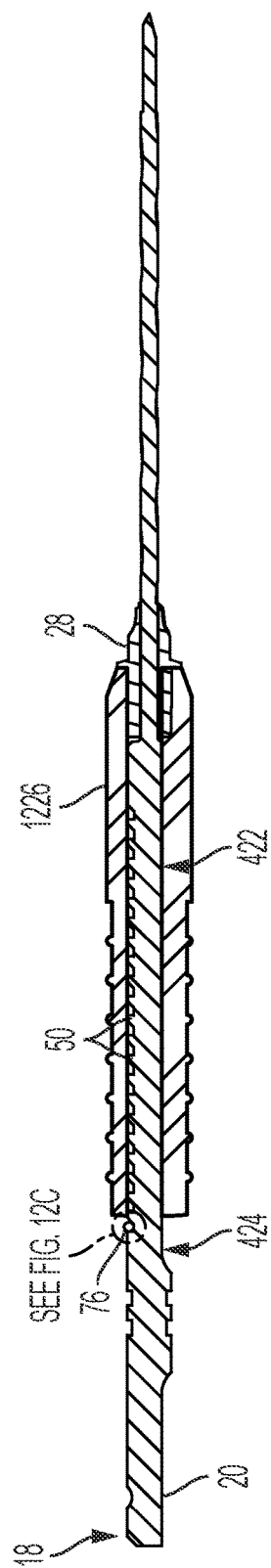
FIG. 12B
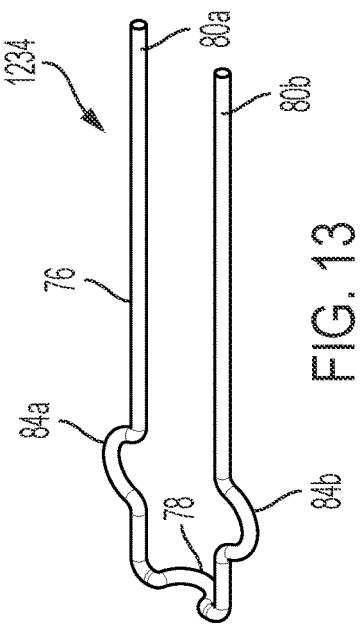
FIG. 13
FIG. 12C

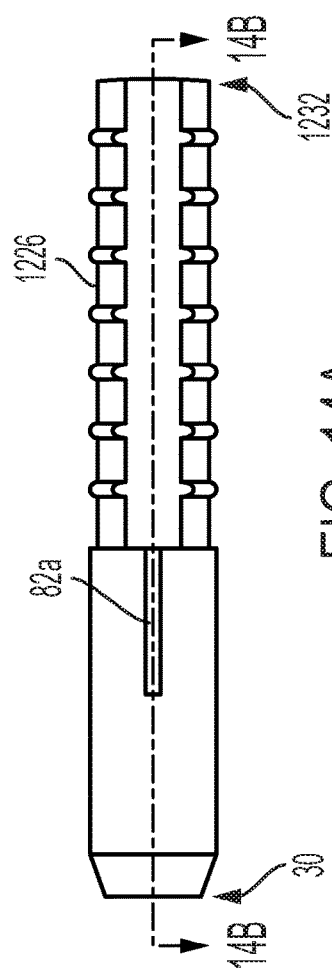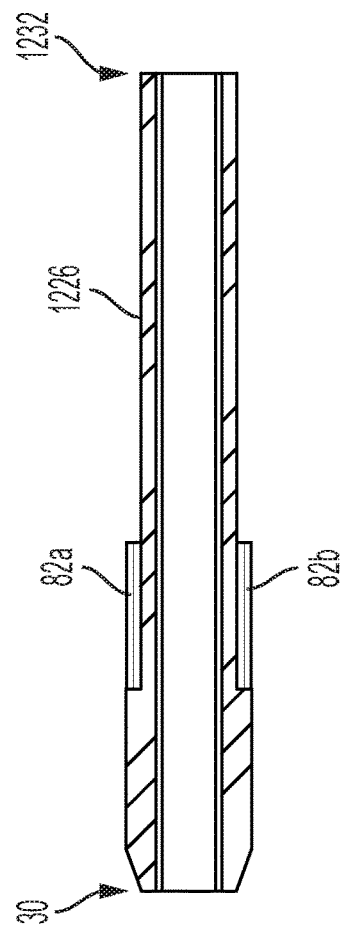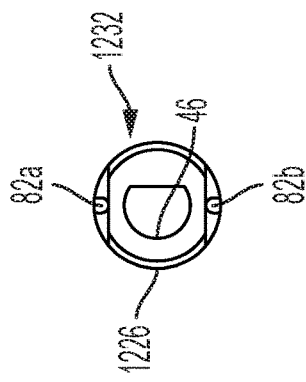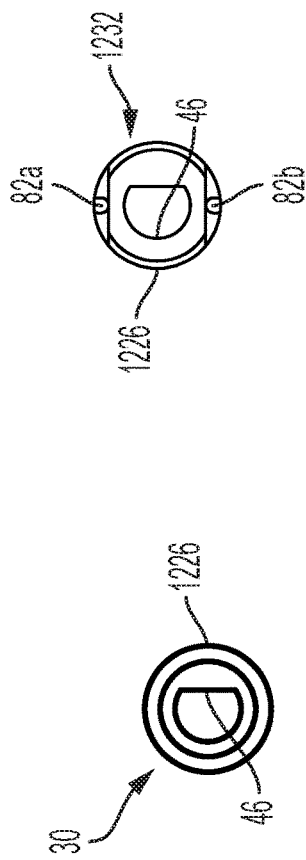

INSTRUMENTS FOR DRILLING HOLES FOR BONE SCREWS

CROSS-REFERENCE TO RELATED APPLICATION

This application claims the benefit of and priority to U.S. Provisional Application No. 62/645,983, filed on Mar. 21, 2018, which is hereby incorporated by reference herein in its entirety.

FIELD

The present disclosure relates to surgical instruments for drilling holes for bone screws.

BACKGROUND

U.S. Pat. No. 1,479,325 discloses a chuck with a means for countersinking a hole made by a drill, and also to provide a gage device for determining the depth of the hole made by the drill, as well as the depth of the countersink.

U.S. Pat. No. 4,341,206 discloses a tool for forming a stepped blind hole in bone for receipt of a fracture reducing and stabilizing surgical implant. The tool comprises a small diameter drill portion axially adjustable with respect to a larger diameter reamer portion. A conical portion includes cutting surfaces to chamfer the entrance of the hole and also includes non-cutting portions which serve to limit penetration of the tool into the bone. The tool is cannulated to allow its use in conjunction with a previously installed Kirschner guide wire.

U.S. Pat. No. 4,549,538 discloses a pin inserter sheath which consists of a plurality of telescoping tubular portions. The sheath is adapted for attachment to a drilling device. A channel extends throughout the elongated telescoping tubular portion which is substantially adapted to the shape of the pin being inserted. The conforming channel provides lateral support to the pin therefore minimizing inflections in the pin as it is being drilled.

U.S. Pat. No. 5,895,389 discloses a surgical drilling guide for guiding a drilling tool, measuring its penetration depth, and protecting surrounding tissue. The guide has a sleeve and a plunger that telescopes within the sleeve. The plunger and the sleeve have axial bores adapted to slidably receive a portion of the tool that protrudes beyond a drill chuck. The extended length of the drilling guide is substantially as long as the length of the protruding portion of the tool, and a maximum extended length of the guide is preferably as long as the protruding portion. As the tool in drilled into a workpiece, the chuck collapses the drilling guide. Gradations on the side of the guide indicate workpiece-penetration depth.

U.S. Pat. No. 7,491,203 discloses an adjustable drill for use in implanting orthopedic screws, such as adjustable compression screws having a separate adjustable head. The adjustable drill comprises a primary drill bit and a countersink drill bit encircling the primary drill bit. The countersink drill bit is configured to selectively slide along the primary drill bit for use in selecting a drill depth. The countersink drill bit is associated with a stop member that is configured to selectively lock the countersink drill bit at one of a plurality of selected positions along the primary drill bit to thereby establish a drill depth. The drill depth corresponds to the size of a selected screw implant, allowing the drill to be used as a trial. The adjustable drill forms a bore having a primary bore and a countersunk entry.

SUMMARY

This Summary is provided to introduce a selection of concepts that are further described herein below in the Detailed Description. This Summary is not intended to identify key or essential features of the claimed subject matter, nor is it intended to be used as an aid in limiting scope of the claimed subject matter.

According to one example of the present disclosure, an instrument for drilling a hole for a bone screw comprises a shaft having a first end, a primary drill fluted portion extending from proximate the shaft's first end toward a second end of the shaft, a shank at the shaft's second end, and a middle portion between the primary drill fluted portion and the shank. At least part of an outer surface of the shaft's middle portion is non-curved. A sleeve surrounds the shaft. The sleeve has an inner surface that is complementary to the outer surface of the shaft's middle portion such that the sleeve is longitudinally slidable with respect to the shaft. The sleeve's inner surface contacts the outer surface of the shaft's middle portion at least at the non-curved part such that the shaft can transmit torque to the sleeve. A countersink drill bit is provided at a first end of the sleeve that is proximate the shaft's primary drill fluted portion. A locking mechanism selectively holds the sleeve in a longitudinally fixed position with respect to the shaft, thereby locating the countersink drill bit at a selected position with respect to the shaft's first end.

According to another example of the present disclosure, an instrument for drilling a hole for a bone screw comprises a shaft having a first end, a primary drill fluted portion extending from proximate the shaft's first end toward a second end of the shaft, a shank at the shaft's second end, and a middle portion between the primary drill fluted portion and the shank. At least part of an outer surface of the shaft's middle portion is non-curved. A sleeve surrounds the shaft. The sleeve has an inner surface that is complementary to the outer surface of the shaft's middle portion such that the sleeve is longitudinally slidable with respect to the shaft. The sleeve's inner surface contacts the outer surface of the shaft's middle portion at least at the non-curved part such that the shaft can transmit torque to the sleeve. A countersink drill bit is provided at a first end of the sleeve that is proximate the shaft's primary drill fluted portion. A locking mechanism selectively holds the sleeve in a longitudinally fixed position with respect to the shaft, thereby locating the countersink drill bit at a selected position with respect to the shaft's first end.

According to another example of the present disclosure, an instrument for drilling a hole for a bone screw comprises a shaft having an end for drilling the hole, an end for connecting to a drill, and a middle portion between the two ends. A sleeve surrounds at least the shaft's middle portion in a longitudinally slidable manner. At least part of an inner surface of the sleeve engages at least part of an outer surface of the shaft's middle portion in a manner that prevents relative rotation between the sleeve and the shaft. A countersink drill bit is provided at an end of the sleeve that is proximate the shaft's drilling end. A locking mechanism is configured to engage with the shaft's middle portion and hold the sleeve in a longitudinally fixed position with respect to the shaft, thereby locating the countersink drill bit at a selected position with respect to the shaft's drilling end.

BRIEF DESCRIPTION OF THE DRAWINGS

The present disclosure is described with reference to the following Figures. The same numbers are used throughout the Figures to reference like features and like components.

FIGS. 3A and 3B illustrate side and top views, respectively, of a third example of a shaft according to the present disclosure.

FIGS. 4A and 4B illustrate side and top views, respectively, of a fourth example of a shaft according to the present disclosure.

FIG. 5 illustrates a first example of an instrument, which includes the shaft of FIGS. 1A and 1B and a first example of a sleeve.

FIGS. 5A and 5B illustrate details of the sleeve and shaft shown in FIG. 5.

FIGS. 12A-12C illustrate a fifth example of an instrument, which includes the shaft of FIG. 7 and a fifth example of a sleeve.

FIG. 13 illustrates a spring-loaded wire for use with the instrument of FIGS. 12A-12C.

FIGS. 14A-14D illustrate details of a fourth example of a sleeve for use with the instrument of FIGS. 12A-12C.

DETAILED DESCRIPTION

Figure 1A:
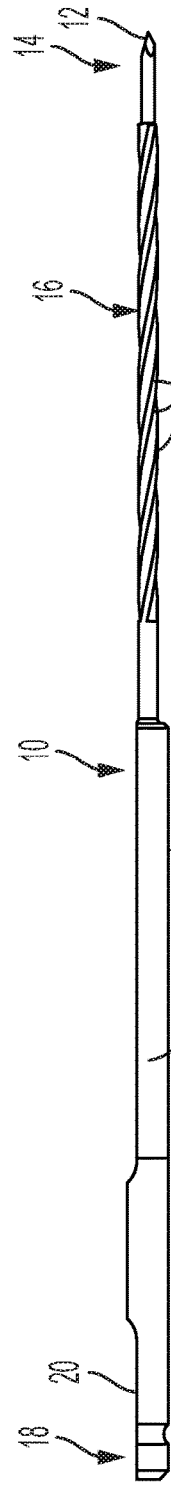
FIGS. 1A and 1B illustrate side and top views, respectively, of a first example of a shaft according to the present disclosure.
Figure 1B:
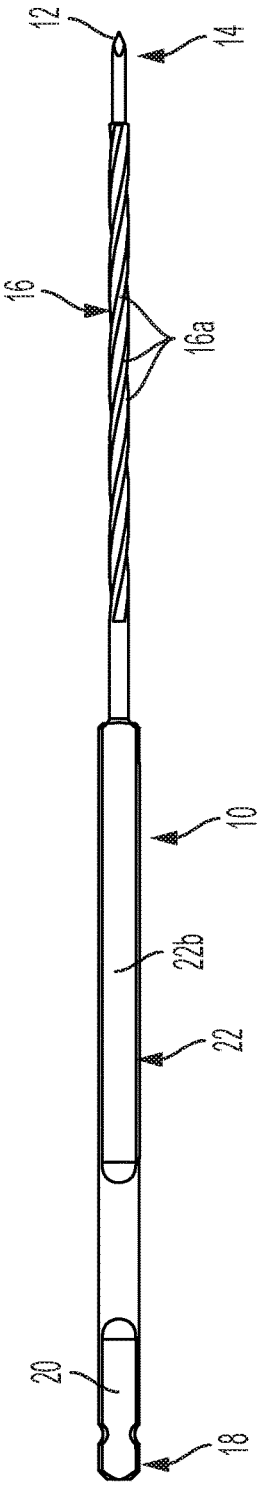

FIG. 1A illustrates a side view of a first example of a portion of an instrument for drilling a hole for a bone screw, while FIG. 1B illustrates a top view thereof. The portion of the instrument shown herein is a shaft 10. The shaft 10 has a trocar tip 12 at a first end 14 thereof. The shaft 10 also includes a primary drill fluted portion 16 (including flutes 16*a*) extending from the trocar tip 12 toward a second end 18 of the shaft 10. A shank 20 is located at the second end 18 of the shaft 10. A middle portion 22 of the shaft 10 is provided between the primary drill fluted portion 16 and the shank 20. The middle portion 22 has a D-shaped cross section. Specifically, the middle portion 22 includes a semi-cylindrical portion 22*a* and a flat portion 22*b*. In the first example of the shaft 10 shown herein, the shaft middle portion 22 has a smooth outer surface.

Figure 2A:
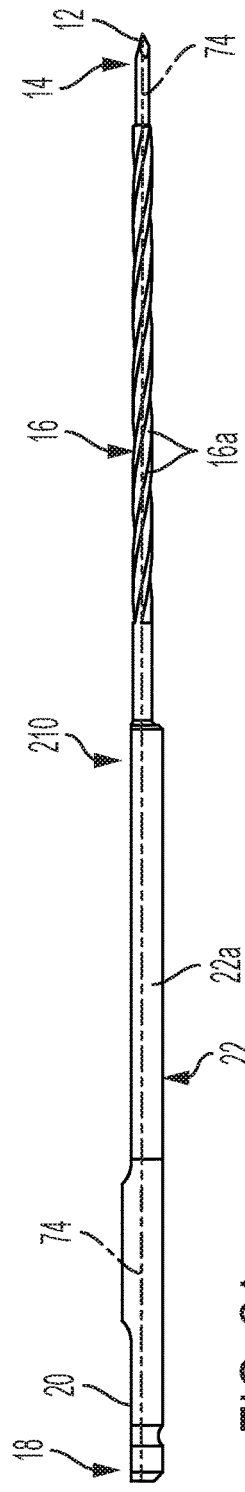
FIGS. 2A and 2B illustrate side and top views, respectively, of a second example of a shaft according to the present disclosure.
Figure 2B:
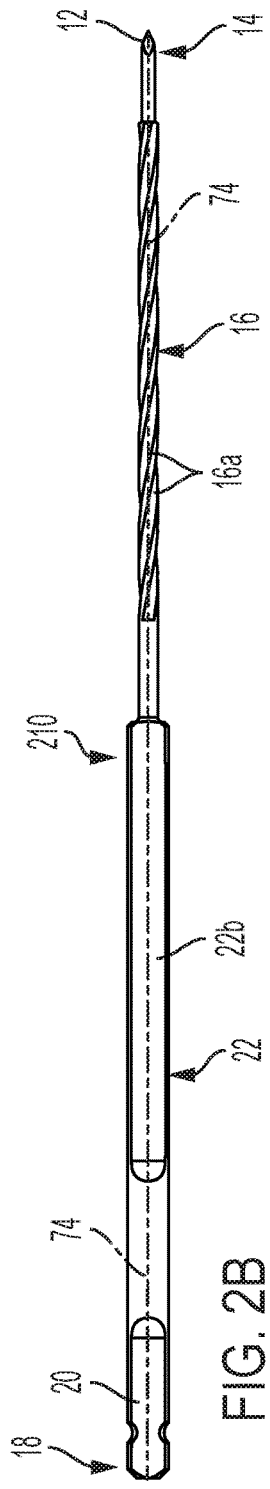

For use of the instrument with a guidewire, the trocar tip 12 and drill fluted portion 16 can be provided with a continuous cannulation 74, which is shown in phantom in the shaft 210 of FIGS. 2A and 2B. The continuous cannulation 74 has an opening at the first end 14 of trocar tip 12 and is placed axially and centrically in the longitudinal direction of the trocar tip 12 and drill fluted portion 16. Depending on the width of the cross-section, the middle portion 22 is provided with a bore or a longitudinal groove in continuation of the continuous cannulation 74 in the trocar tip 12 and drill fluted portion 16. This allows the instrument to be used to prepare boreholes around a placed K-wire for insertion of a wire-guided cannulated screw into the bone. The internal diameter of the cannulation 74 can be sized to fit standard K-wire sizes, such as 0.035 inches, 0.045 inches, 0.062 inches, etc. Note that although the cannulation 74 is shown in an embodiment of the shaft 210 that is similar to that shown in FIGS. 1A and 1B, the cannulation 74 could be provided in any of the shafts shown and described herein below.

In a third example of the shaft 310 shown in FIGS. 3A and 3B, the middle portion 322 of the shaft 310 comprises a threaded outer surface. Meanwhile, the fourth example of the shaft 410 shown in FIGS. 4A and 4B includes a middle portion 422 comprising a series of angled ratchet grooves. The remainder of the portions of the third and fourth examples of the shaft 310, 410 are the same as those described hereinabove with respect to the first example of FIGS. 1A and 1B.

Turning to FIG. 5, a first example of an instrument 24 is shown therein. The instrument 24 includes the shaft 10 of FIGS. 1A and 1B. Here, a sleeve 26 is provided surrounding the shaft 10. As shown in FIG. 5B, the sleeve 26 has a D-shaped inner surface that slides along the middle portion 22 of the shaft 10. (See also FIG. 6B, wherein the D-shaped inner surface is labeled 46.) A countersink drill bill 28 is provided at a first end 30 of the sleeve 26 that is proximate the primary drill fluted portion 16. A second end 32 of the sleeve 26 is opposite the first end 30. The second end 32 of the sleeve 26 is provided with a locking mechanism 34 that selectively holds the sleeve 26 in a fixed position with respect to the shaft 10. When the locking mechanism 34 is not engaged, the sleeve 26 may slide freely along the shaft 10 in order to adjust the relative location of the countersink drill bit 28 with respect to the first end 14 of the shaft 10. When the locking mechanism 34 is engaged, it fixes the countersink drill bit 28 at a selected position with respect to the first end 14 of the shaft 10.

Referring to FIGS. 5A and 5B, the locking mechanism 34 comprises a set screw 36 that extends transversely through an outer surface of the sleeve 26 and is configured to contact an outer surface of the middle portion 22 of the shaft 10. More specifically, the set screw 36 contacts the flat portion 22*b* of the middle portion 22 of the shaft 10. In one example, the set screw 36 may have the same hex (or torx) size as the screw drive used to drive the shaft 10. Note that laser markings 38 can be provided to indicate the overall screw length, i.e., the length from the tip of the drill flutes 16*a* to a point on the countersink drill bit 28. The sleeve 26 and locking mechanism 34 of FIGS. 5A and 5B could also be used with the shaft 210 of FIGS. 2A and 2B.

Figure 6:
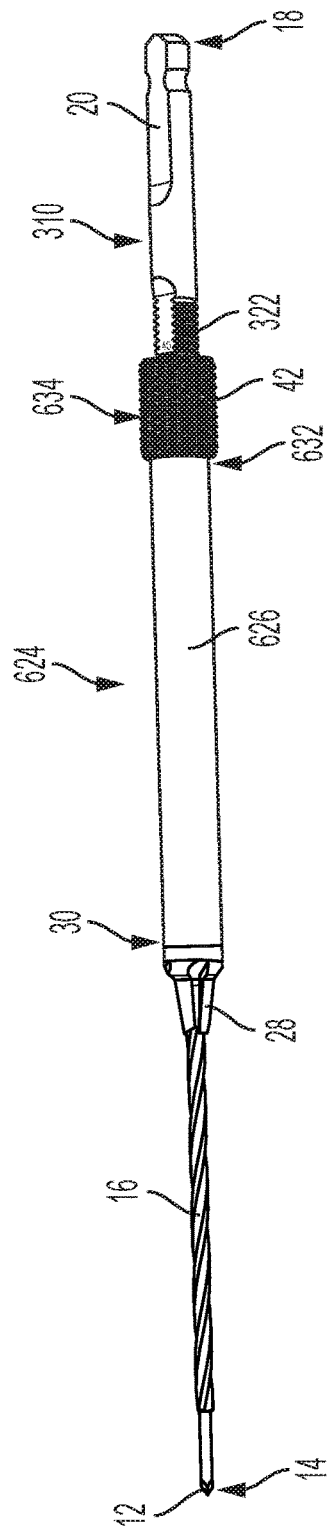
FIG. 6 illustrates a second example of an instrument, which includes the shaft of FIGS. 3A and 3B and a second example of a sleeve.
Figure 6B:
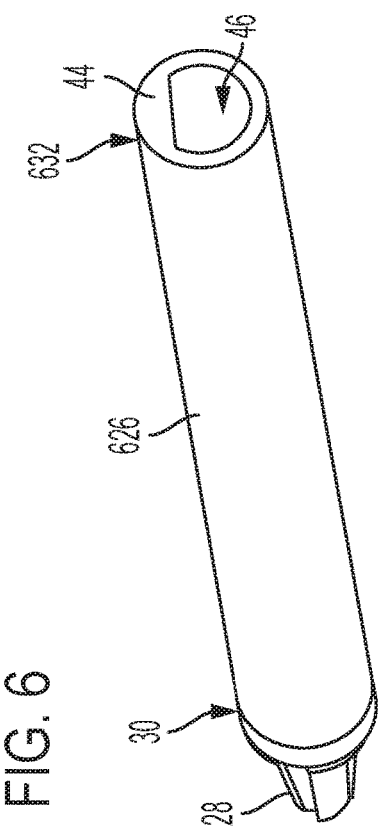
FIGS. 6A-6D illustrate details of portions of the instrument shown in FIG. 6.

FIG. 6 illustrates a second example of an instrument 624, which includes the third example of the shaft 310 shown in FIGS. 3A and 3B. As noted hereinabove and shown in FIG. 6A, the middle portion 322 of the shaft 310 comprises a series of threads 40. Here, the locking mechanism 634 comprises a nut 42 having a threaded inner surface 42*a*. See FIG. 6C. The threaded inner surface 42*a* is engaged with the series of threads 40 of the shaft 310, as shown in FIG. 6A, and the nut 42 is located proximate the second end 632 of the sleeve 626 that is opposite the countersink drill bit 28. When the nut 42 is rotated toward the second end 18 of the shaft 310, the sleeve 626 and countersink drill bit 28 can be moved further away from the first end 14 of the shaft 310. Conversely, as the nut 42 is rotated closer toward the first end 14 of the shaft 310, the countersink drill bit 28 and sleeve 626 are moved closer to the first end 14, thereby decreasing the drill depth. The second end 632 of the sleeve 626 has a flat end surface 44 (FIG. 6B) for abutting the end surface of the nut 42. Note that the D-shaped inner surface 46 of the sleeve is also shown in FIG. 6B.

Figure 6D:
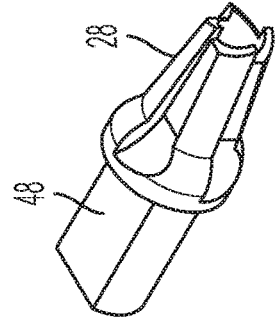
Figure 6A:
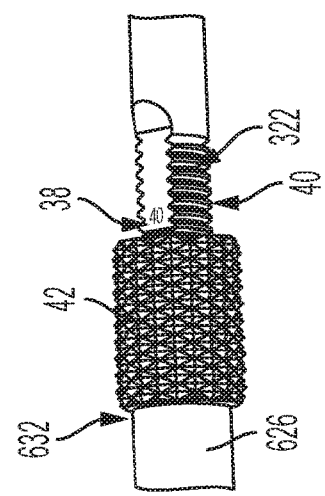
Figure 6C:
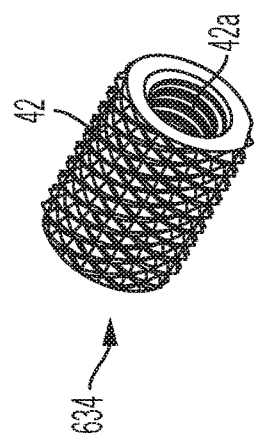

The countersink drill bit 28, FIG. 6D, can be made of stainless steel and can be press fit into the sleeve 626, which may be a molded body, by way of a shank fitting 48. The shank fitting 48 also has a D-shaped cross section in order to fit snugly within the sleeve 626 at the first end 30 thereof. Note that the same press fit design could be used for the countersink drill bit 28 and sleeve 26 of the first example (described hereinabove) and for the countersink drill bit 28 and sleeves 726, 1126, and 1226 of the third, fourth, and fifth examples to be described herein below. In another example, the countersink drill bit 28 and the sleeve 26, 626, 726, 1226 could be a single, integral part.

Figure 7:
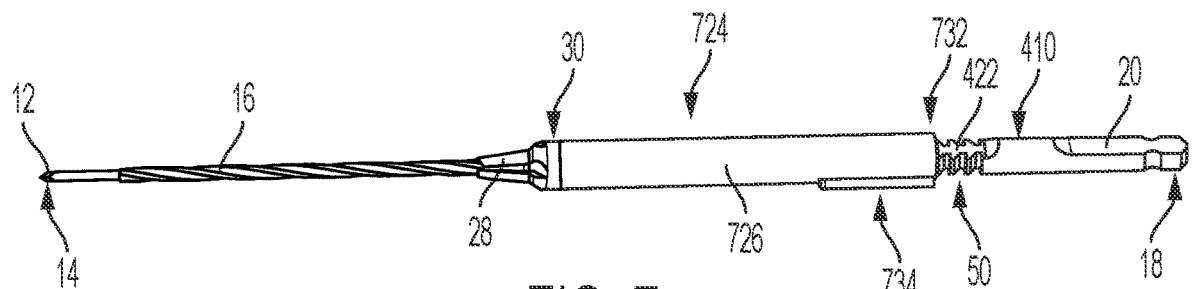
FIG. 7 illustrates a third example of an instrument, which includes the shaft of FIGS. 4A and 4B and a third example of a sleeve.
Figure 7A:
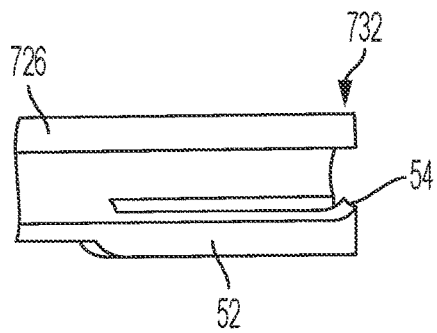
FIGS. 7A-7C illustrate details of the third example of the instrument shown in FIG. 7.
Figure 7B:
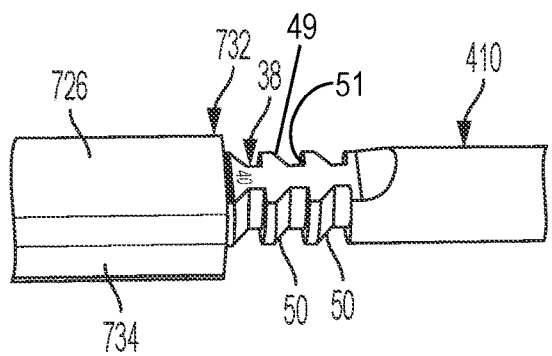
Figure 7C:
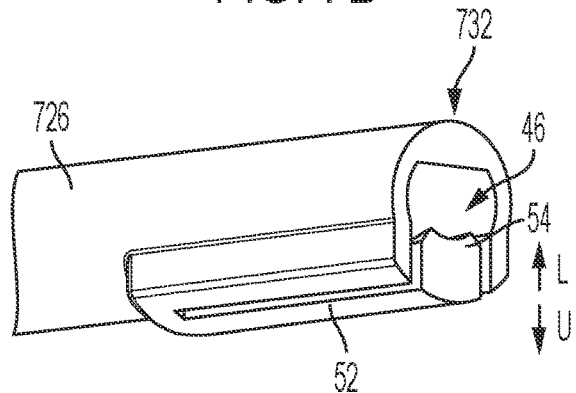

FIG. 7 illustrates a third example of an instrument 724, which includes the fourth example of the shaft 410 illustrated in FIGS. 4A and 4B. In this example, the middle portion 422 of the shaft 410 comprises a series of angled ratchet grooves 50. As shown in FIGS. 7A-7C, the second end 732 of the sleeve 726 includes a finger 52 that can be moved axially away from and back towards a central axis of the sleeve 726. The finger 52 on the sleeve 726 has an axially inwardly facing ratchet tooth 54, and the series of angled ratchet grooves 50 on the shaft 410 are configured to receive the ratchet tooth 54. Thus, the finger 52 and ratchet tooth 54 are a third example of the locking mechanism 734.

When the ratchet tooth 54 is moved in the direction of the arrow L (FIG. 7C) by way of an inherent spring force, the ratchet tooth 54 is fully engaged with a select one of the ratchet grooves 50, thereby locking the position of the sleeve 726 with respect to the first end 14 of the shaft 410. When the ratchet tooth 54 is moved axially away from the shaft 410, in the direction of the arrow U, the sleeve 726 is free to move along the shaft 410 in order to adjust the drill depth. Note that due to the angling of the surfaces 49 on the ratchet grooves 50, the sleeve 726 can be easily moved toward the first end 14 of the shaft 410, as the ratchet tooth 54 slides over the angled surfaces 49 of the ratchet grooves 50 toward the first end 14 of the shaft 410. However, in order to disengage the ratchet tooth 54 from the ratchet grooves 50 and move the sleeve 726 toward the second end 18 of the shaft 410, the ratchet tooth 54 must be pulled out of the ratchet grooves 50 by the user, past the surface 51 of the ratchet groove 50 that is perpendicular to the longitudinal axis of the shaft 410. Various examples of how such disengagement or release of the ratchet tooth 54 from the ratchet grooves 50 can be accomplished are shown in FIGS. 8A-10B.

Figure 8A:
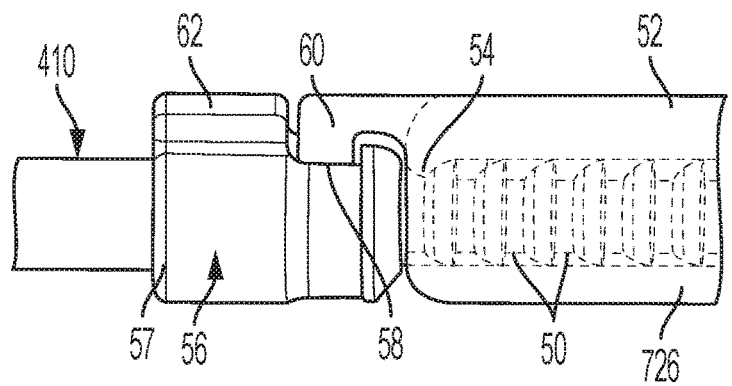
FIGS. 8A-8E illustrate a release mechanism that can be used with the instrument of FIG. 7.
Figure 8B:
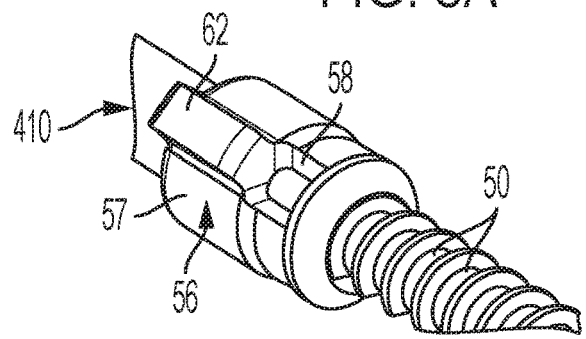
Figure 8C:
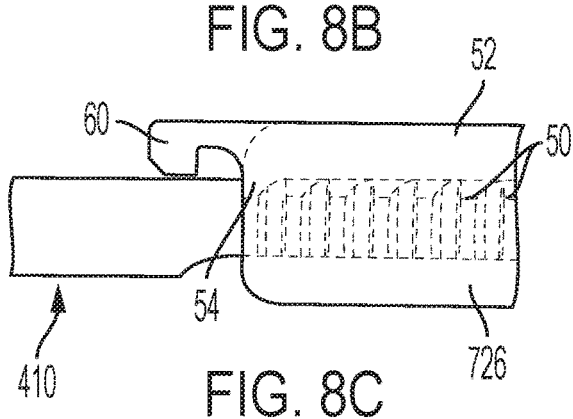
Figure 8D:
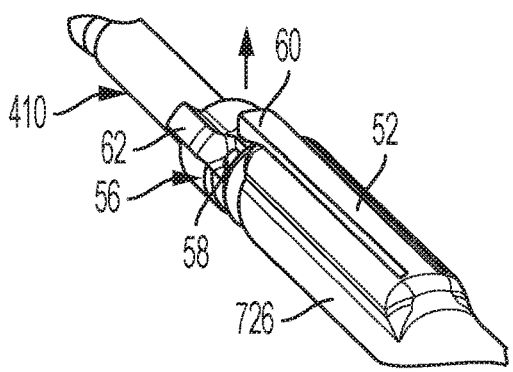
Figure 8E:
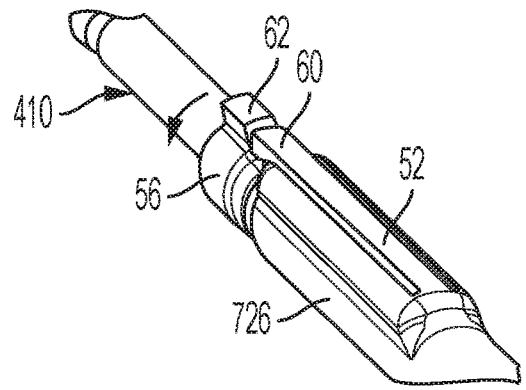
Figure 9A:
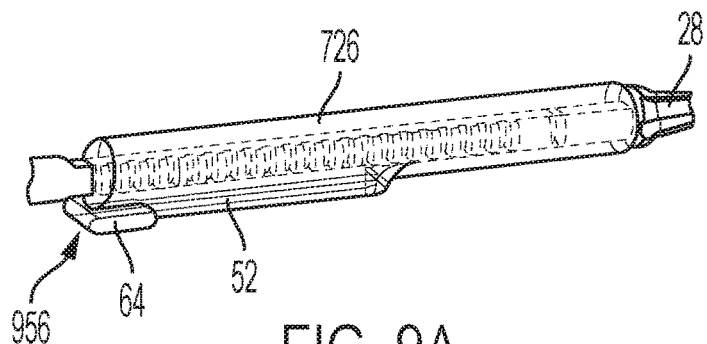
FIG. 9A-9D illustrate another example of a release mechanism that can be used with the instrument of FIG. 7.
Figure 9B:
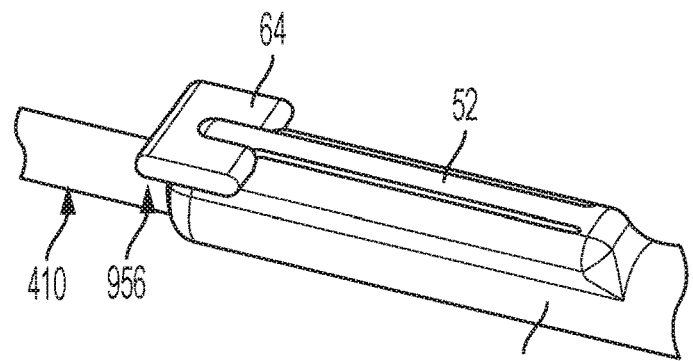
Figure 9C:
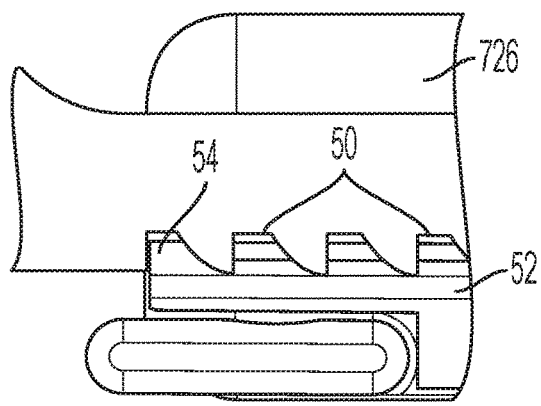
Figure 9D:
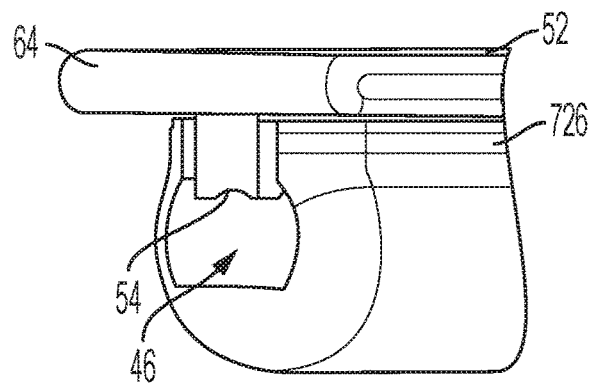

FIGS. 8A-8E illustrate one example of a release mechanism 56 for the ratchet tooth 54, which works in a rotational manner. The release mechanism 56 comprises a sleeve 57 having a groove, hollow, or indentation 58 for receiving a locking tab 60 that is attached to the finger 52 and ratchet tooth 54. As shown in FIG. 8A, when the release mechanism 56 is rotated such that the locking tab 60 is seated within the indentation 58, the locking tab 60 and finger 52 are moved by inherent spring force such that the connected ratchet tooth 54 is moved into engagement with the ratchet grooves 50. The release mechanism 56 can be rotated about the shaft 410 by way of a handling tab 62, as shown by the arrow in FIG. 8E. When the release mechanism 56 is rotated such that the locking tab 60 is not located within the indentation 58, the locking tab 60 is pressed outwardly from the shaft 410 as shown by the arrow in FIG. 8D. Correspondingly, the finger 52 and ratchet tooth 54 are moved axially away from the shaft 410 and the ratchet tooth 54 is disengaged from the ratchet grooves 50.

FIGS. 9A-9D illustrate an example in which the ratchet tooth 54 is released from the ratchet grooves 50 by a second example of a release mechanism 956, which in this case is a handling tab 64. The handling tab 64 includes a pair of wide wings that allow for easy gripping by the user, who moves the handling tab 64 and thus the finger 52 and ratchet tooth 54 connected thereto toward and away from the ratchet grooves 50 in order to engage and disengage the ratchet tooth 54 with and from the ratchet grooves 50.

Figure 10A:
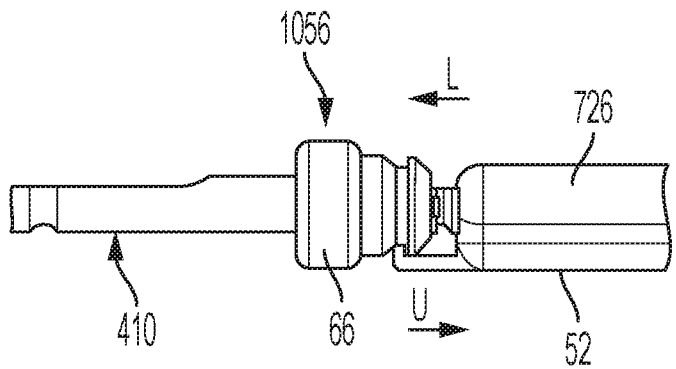
FIGS. 10A and 10B illustrate another example of a release mechanism that can be used with the instrument of FIG. 7.
Figure 10B:
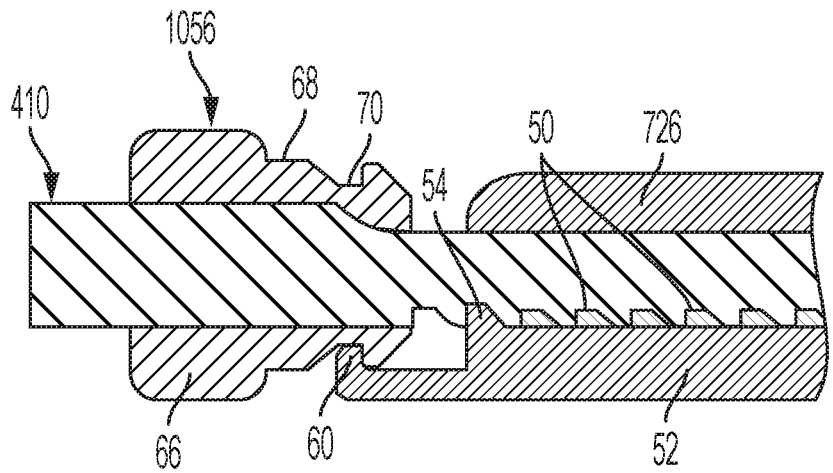

FIGS. 10A and 10B show another example of a release mechanism 1056, which here is in the form of a stepped sleeve 66. The stepped sleeve 66 can be moved toward and away from the sleeve 726 in order to engage and disengage the ratchet tooth 54 from the ratchet grooves 50. When the stepped sleeve 66 is moved in the direction of arrow U, the locking tab 60 moves to a circumferential step 68 having a larger diameter, thereby forcing the locking tab 60, and connected finger 52 and ratchet tooth 54, axially away from the shaft 410. Thus, the ratchet tooth 54 disengages from the ratchet grooves 50. On the other hand, when the stepped sleeve 66 is thereafter moved in the direction of arrow L, the locking tab 60 slides into a groove 70 having a smaller diameter than that of the step 68. This allows the locking tab 60 to move axially inwardly toward the shaft 410. Simultaneously, the finger 52 moves in toward the shaft 410, and the ratchet tooth 54 engages with the ratchet grooves 50.

FIGS. 12A and 12B show a top and a cross-sectional view, respectively, of another example of an instrument 1224 having another example of a sleeve 1226 and locking mechanism 1234 associated therewith. The instrument 1224 includes the shaft 410 having angled ratchet grooves 50, as shown in FIGS. 4A and 4B. In this example, however, the locking mechanism 1234 comprises a spring-loaded wire 76 having a locking portion 78 that at least partially surrounds the outer surface of the shaft's middle portion 422 and is configured to be received in one of the ratchet grooves 50 (see FIG. 12C). The wire 76 also includes two legs 80*a*, 80*b*, as shown in FIG. 13, each of which is configured to be received in a respective slot 82*a*, 82*b* (FIGS. 14A, 14B, 14D) on either side of the sleeve 1226 in order to hold the wire 76 on the instrument 1224. Referring now to FIGS. 12A and 13, two handles 84*a*, 84*b* formed on either side of the wire 76 can be used to release the locking portion 78 from the ratchet groove 50, such as by pressing the handles 84*a*, 84*b* inwardly toward the sleeve 1226. Such inward pressing against the spring force of the wire 76 causes the locking portion 78 to move out of the ratchet groove 50, such that the sleeve 1226, and thus countersink drill bit 28, can be advanced toward the first end 14 of the shaft 410 or retracted toward the second end 18 thereof. Releasing the inward force on the handles 84*a*, 84*b* causes the spring force of the wire 76 to move the locking portion 78 back into a ratchet groove 50 at the new location of the sleeve 1226.

FIGS. 14C and 14D show end views of the sleeve 1226 of the instrument 1224. Here, the D-shaped cross-sectional shape of the inner surface 46 of the sleeve 1226 can easily be seen. As noted hereinabove, the shaft 410 has an outer surface with a cross-sectional shape that can fit within the sleeve 1226. Specifically, the shaft 410 has a D-shaped cross-section that is slightly smaller than that of the inner surface 46 of the sleeve 1226. Note that the sleeves of the other embodiments described hereinabove have the same end view from the end 30.

In each of the above designs utilizing a ratchet tooth 54, the ratchet tooth 54 may be from about 0.55 mm to about 1 mm in height, and preferably about 0.85 mm. In one example, the corresponding ratchet grooves 50 may be designed such that there is nominal interference between the ratchet tooth 54 and the ratchet grooves 50. For example, the ratchet grooves 50 could be between about 0.45 mm to about 0.9 mm, and preferably about 0.75 mm. In one example, the ratchet tooth 54 may be capable of withstanding force of up to 25 N. Note that the tooth design described herein above is merely exemplary, and the ranges could vary outside those specified herein.

Therefore, the instruments 24, 624, 724, 1224 described herein include a shaft 10, 210, 310, 410 having a first end 14, a primary drill fluted portion 16 extending from proximate the shaft's first end 14 toward a second end 18 of the shaft 10, 210, 310, 410, a shank 20 at the shaft's second end 18, and a middle portion 22, 222, 322, 422 between the primary drill fluted portion 16 and the shank 20. At least part of an outer surface of the shaft's middle portion 22, 222, 322, 422 is non-curved. A sleeve 26, 626, 726, 1226 surrounds the shaft 10, 210, 310, 410. The sleeve 26, 626, 726, 1226 has an inner surface that is complementary to the outer surface of the shaft's middle portion 22, 222, 322, 422 such that the sleeve 26, 626, 726, 1226 is longitudinally slidable with respect to the shaft 10, 210, 310, 410. The sleeve's inner surface contacts the outer surface of the shaft's middle portion 22, 222, 322, 422 at least at the non-curved part 22*b* such that the shaft 10, 210, 310, 410, which is driven by a drill at shank 20, can transmit torque to the sleeve 26, 626, 726, 1226. A countersink drill bit 28 is provided at a first end 30 of the sleeve 26, 626, 726, 1226 that is proximate the shaft's primary drill fluted portion 16. A locking mechanism 34, 634, 734, 1234 selectively holds the sleeve 26, 626, 726, 1226 in a longitudinally fixed position with respect to the shaft 10, 210, 310, 410, thereby locating the countersink drill bit 28 at a selected position with respect to the shaft's first end 14.

Also disclosed are instruments 24, 624, 724, 1224 for drilling a hole for a bone screw comprising a shaft 10, 210, 310, 410 having a first end 14, a primary drill fluted portion 16 extending from proximate the shaft's first end 14 toward a second end 18 of the shaft 110, 210, 310, 410, a shank 20 at the shaft's second end 18, and a middle portion 22, 222, 322, 422 between the primary drill fluted portion 16 and the shank 20. At least part of an outer surface of the shaft's middle portion 22, 222, 322, 422 is non-curved. A sleeve 26, 626, 726, 1226 surrounds the shaft 10, 210, 310, 410. The sleeve 26, 626, 726, 1226 has an inner surface that is complementary to the outer surface of the shaft's middle portion such that the sleeve 26, 626, 726, 1226 is longitudinally slidable with respect to the shaft 10, 210, 310, 410. The sleeve's inner surface contacts the outer surface of the shaft's middle portion 22, 222, 322, 422 at least at the non-curved part such that the shaft 10, 210, 310, 410 can transmit torque to the sleeve 26, 626, 726, 1226. A countersink drill bit 28 is provided at a first end 30 of the sleeve 26, 626, 726, 1226 that is proximate the shaft's primary drill fluted portion 16. A locking mechanism 34, 634, 734, 1234 selectively holds the sleeve 26, 626, 726, 1226 in a longitudinally fixed position with respect to the shaft 10, 210, 310, 410, thereby locating the countersink drill bit 28 at a selected position with respect to the shaft's first end 14.

Also disclosed are instruments 24, 624, 724, 1224 for drilling a hole for a bone screw comprising a shaft 10, 210, 310, 410 having an end 14 for drilling the hole, an end 18 for connecting to a drill, and a middle portion 22, 222, 322, 422 between the two ends 14, 18. A sleeve 26, 626, 726, 1226 surrounds at least the shaft's middle portion 22, 222, 322, 422 in a longitudinally slidable manner. At least part of an inner surface of the sleeve 26, 626, 726, 1226 engages at least part of an outer surface of the shaft's middle portion 22, 222, 322, 422 in a manner that prevents relative rotation between the sleeve 26, 626, 726, 1226 and the shaft 10, 210, 310, 410. A countersink drill bit 28 is provided at an end 30 of the sleeve 26, 626, 726, 1226 that is proximate the shaft's drilling end 14. A locking mechanism 34, 634, 734, 1234 is configured to engage with the shaft's middle portion 22, 222, 322, 422 and hold the sleeve 26, 626, 726, 1226 in a longitudinally fixed position with respect to the shaft 10, 210, 310, 410, thereby locating the countersink drill bit 28 at a selected position with respect to the shaft's drilling end 14.

According to some examples of the shaft 310, 410, an outer surface of the shaft's middle portion 322, 422 includes a series of ridges with which the locking mechanism 634, 734, 1234 is configured to engage so as to allow for incremental adjustment of the countersink drill bit 28 with respect to the shaft's first end 14. In the example of FIGS. 3A, 3B, and 6-6D, the series of ridges comprises a series of threads 40, and the locking mechanism 634 comprises a nut 42 having a threaded inner surface 42*a* engaged with the threads 40 on the outer surface of the shaft's middle portion 322, the nut 42 being located proximate a second end 632 of the sleeve 626 that is opposite the countersink drill bit 28. In another example, as shown in FIGS. 4A, 4B and 7-10B, the series of ridges comprises a series of angled ratchet grooves 50, and the locking mechanism 734 comprises a finger 52 on the sleeve 726 having an axially-inwardly facing ratchet tooth 54 configured to be received in one of the ratchet grooves 50. In these examples, the instrument 724 further includes a release mechanism 56, 956, 1056 that when actuated lifts the finger 52 out of the ratchet groove 50. In still other examples, the series of ridges comprises a series of angled ratchet grooves 50, and the locking mechanism 1234 comprises a spring-loaded wire 76 having a locking portion 78 that at least partially surrounds the outer surface of the shaft's middle portion 422 and is configured to be received in one of the ratchet grooves 50.

In the above-noted examples, the locking mechanism 34, 634, 734, 1234 is provided proximate a second end of the sleeve 26, 626, 726, 1226 that is opposite the countersink drill bit 28. This provides for easy handling of the locking mechanism while the instrument is in use. However, in some examples, the locking mechanism can be provided at the first end 30 of the sleeve 26, 626, 726, 1226 or along a middle area of the sleeve 26, 626, 726, 1226.

In each of the above examples, advantages are provided in that the torque transmission mechanism and locking mechanism are proximate the drill connector area at the shank 20. This allows for larger diameter features for more robust torque transmission and locking. Additionally, larger features are easier and therefore lower cost to manufacture. The present examples each have torque transmission that is separated from the axial locking function. In contrast, instruments that achieve both torque transmission and axial locking simultaneously, with the same mechanism, do not necessarily perform well, and separating of these functions allows for more flexibility in how each function is achieved.

Each of the above examples is of a shaft 10, 210, 310, 410 including a middle portion 22, 222, 322, 422 having D-shaped cross section, which provides for robust torque transmission between the driven shaft and the countersink drill bit 28 provided on the sleeve 26, 626, 726, 1226. For purposes of torque transmission, the sleeve's inner surface is complementary to the outer surface of the shaft's middle portion 22, 222, 322, 422. The sleeve's inner surface and the shaft's middle portion could have the same cross-sectional shape (here, a D-shape), or the cross-sectional shapes could be different from one another. In the latter example, the shaft's middle portion 22, 222, 322, 422 would still need to be shaped such that it could be received in the sleeve 26, 626, 726, 1226 and the two parts could slide longitudinally with respect to one another. However, the shaft 10, 210, 310, 410 might have only the flat portion 22b for engaging with the inner surface of the sleeve 26, 626, 726, 1226, but might not have the semi-cylindrical portion 22a. Instead, another flat portion or a differently shaped portion could be provided opposite the flat portion 22b, so long as that differently shaped portion fit and slid within the sleeve 26, 626, 726, 1226. Additionally, note that the shaft and sleeve need not have D-shaped cross sections as shown herein, but could instead have any shape of complementary non-curved surfaces for purposes of torque transmission. For example, the shaft and sleeve may have one or a series of splines, one or a series of ridges, or other similar non-continuous surfaces that transfer a torque from the shaft to the sleeve. Other examples of cross-sectional shapes that could be used include a double, back-to-back D-shape; a triangular shape; a square or rectangular shape; a hexagonal shape; or any other shape having at least one flat surface for aiding in torque transfer. It should be understood that the inner surface 46 of the sleeve 26, 626, 726, 1226 would have a corresponding cross-sectional shape to fit around the shaft 10, 210, 310, 410. In general, the concepts noted hereinabove each employ simple to use locking mechanisms and release mechanisms for those locking mechanisms, which allow or prevent relative sliding between the sleeves 26, 626, 726, 1226 and shafts, 10, 210, 310, 410 for adjustment of the drill depth.

Each of the above exemplary instruments 24, 624, 724, 1224 also provides an advantage in that the trocar tip 12 (acting as a guidewire), the primary drill fluted portion 16, and the adjustable countersink drill bit 28 are provided on the same instrument, without any need to swap components. The lack of a need to swap components and/or instruments while drilling a hole for a bone screw saves a great amount of time in the operating room, and also eliminates the possibility that the operator will utilize an incorrectly sized tool. For example, the operator can feel once the drill engages and drills through the cortex, after which the operator can slide down the sleeve, noting laser markings 38 serving as a depth gauge, and continue with the countersink. Using one tool, all these steps can be simply completed.

Figure 11:
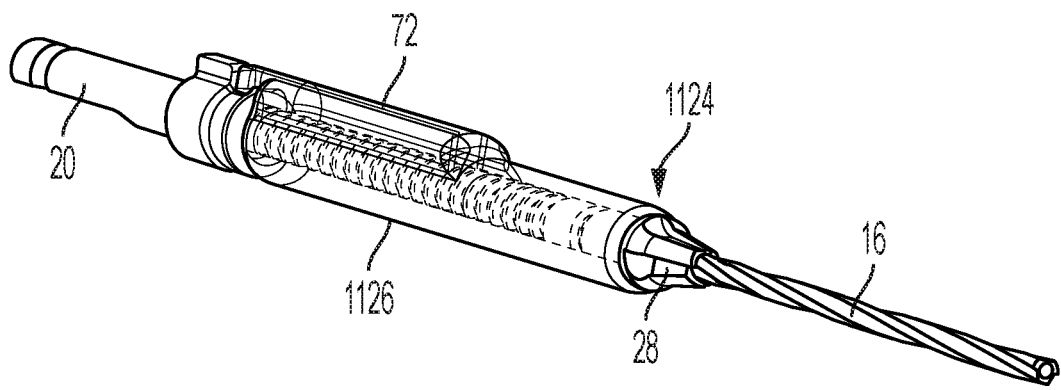
FIG. 11 illustrates a fourth example of an instrument, which includes the shaft of FIG. 7 and a fourth example of a sleeve.

Additionally, note that although it is not necessary to first install a guidewire before utilizing the instruments 24, 624, 724, 1224 of the present disclosure due the presence of the trocar tip 12, which acts as guidewire, in some instances it may be desirable to allow for use of the instrument with a guidewire. Thus, the sleeve 1126 could be provided with a cannulation 72 in the longitudinal direction, see FIG. 11, which allows for insertion of a Kirshner wire that has been placed before the hole is been drilled into the bone. Use of a K wire for guidance and fixing thereof within the bone prior to drilling of a hole is well known, and will not be further described herein. Note that in this fourth example of the instrument 1124, no trocar tip 12 is provided. In this example, the internal diameter of the cannulation 72 can be sized to fit standard K-wire sizes, such as 0.035 inches, 0.045 inches, 0.062 inches, etc. This allows an operator to use K-wires already available to the operator, while still realizing the advantages of the calibrated depth gauge on the shaft of the present drill. Note that the cannulation 72 could be provided on the sleeve 26, 626, 726, 1226 of any of the embodiments described hereinabove.

In the above description, certain terms have been used for brevity, clarity, and understanding. No unnecessary limitations are to be inferred therefrom beyond the requirement of the prior art because such terms are used for descriptive purposes and are intended to be broadly construed. The different assemblies and method steps described herein may be used alone or in combination with other assemblies and methods. It is to be expected that various equivalents, alternatives and modifications are possible within the scope of the appended claims.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. An instrument for drilling a hole for a bone screw, the instrument comprising:
 a shaft having:
  a first end;
  a primary drill fluted portion extending from proximate the shaft's first end toward a second end of the shaft;
  a shank at the shaft's second end; and
  a middle portion between the primary drill fluted portion and the shank, at least part of an outer surface of the shaft's middle portion being non-curved;
 a sleeve surrounding the shaft, the sleeve having an inner surface that is complementary to the outer surface of the shaft's middle portion such that the sleeve is longitudinally slidable with respect to the shaft, wherein the sleeve's inner surface contacts the outer surface of the shaft's middle portion at least at the non-curved part such that the shaft can transmit torque to the sleeve;
 a countersink drill bit provided at a first end of the sleeve that is proximate the shaft's primary drill fluted portion; and
 a locking mechanism that selectively holds the sleeve in a longitudinally fixed position with respect to the shaft, thereby locating the countersink drill bit at a selected position with respect to the shaft's first end;
 wherein the outer surface of the shaft's middle portion further comprises a series of angled ratchet grooves with which the locking mechanism is configured to engage so as to allow for incremental adjustment of the countersink drill bit with respect to the shaft's first end; and wherein a given ratchet groove in the series of ratchet grooves has a first surface proximate the first end of the shaft that is non-perpendicular with respect to a longitudinal axis of the shaft and over which the locking mechanism slides as the sleeve is moved toward the first end of the shaft and has a second surface proximate the second end of the shaft that is perpendicular to the longitudinal axis of the shaft such that the locking mechanism must be removed from the given ratchet groove before the sleeve can be moved toward the second end of the shaft.

2. The instrument of claim 1, wherein the locking mechanism comprises a finger on the sleeve having an axially-inwardly facing ratchet tooth configured to be received in one of the ratchet grooves.

3. The instrument of claim 2, further comprising a release mechanism that when actuated lifts the ratchet tooth of the finger out of the ratchet groove.

4. The instrument of claim 1, wherein the locking mechanism comprises a spring-loaded wire having a locking portion that at least partially surrounds the outer surface of the shaft's middle portion and is configured to be received in one of the ratchet grooves.

5. The instrument of claim 4, wherein the wire has two legs, first ends of which are configured to be coupled to the sleeve and second ends of which are connected by the locking portion, and wherein the locking mechanism further comprises handles formed from the wire on either side of the locking portion, the locking mechanism being configured such that force applied to the handles causes the locking portion to be removed from the ratchet groove.

6. The instrument of claim 1, wherein the locking mechanism is provided proximate a second end of the sleeve that is opposite the countersink drill bit.

7. An instrument for drilling a hole for a bone screw, the instrument comprising:
a shaft having:
a first end;
a primary drill fluted portion extending from proximate the first end of the shaft toward a second end of the shaft;
a shank at the second end of the shaft; and
a middle portion between the primary drill fluted portion and the shank, the middle portion having a cross-sectional shape with at least one flat surface;
a sleeve surrounding the shaft, the sleeve having an inner surface with the same cross-sectional shape as that of the middle portion, which inner surface slides along the middle portion of the shaft;
a countersink drill bit provided at a first end of the sleeve that is proximate the primary drill fluted portion; and
a locking mechanism that selectively holds the sleeve in a fixed position with respect to the shaft, for locating of the countersink drill bit at a selected position with respect to the first end of the shaft;
wherein an outer surface of the shaft's middle portion comprises a series of ratchet grooves with which the locking mechanism is configured to engage so as to allow for incremental adjustment of the countersink drill bit with respect to the first end of the shaft;
wherein the locking mechanism comprises a spring-loaded wire having two legs, first ends of which are configured to be coupled to the sleeve and second ends of which are connected by a locking portion that at least partially surrounds the outer surface of the shaft's middle portion and is configured to be received in one of the ratchet grooves; and
wherein the locking mechanism further comprises two handles formed along the respective legs of the wire on either side of the locking portion, the locking mechanism being configured such that force applied to the handles causes the locking portion to be released from the ratchet groove.

8. The instrument of claim 7, wherein the cross-sectional shape of the middle portion is a D-shape.

9. The instrument of claim 7, wherein a given ratchet groove in the series of ratchet grooves has a first surface proximate the first end of the shaft that is non-perpendicular with respect to a longitudinal axis of the shaft and over which the locking mechanism slides as the sleeve is moved toward the first end of the shaft and has a second surface proximate the second end of the shaft that is perpendicular to the longitudinal axis of the shaft such that the locking mechanism must be released from the given ratchet groove before the sleeve can be moved toward the second end of the shaft.

10. An instrument for drilling a hole for a bone screw, the instrument comprising:
a shaft having an end for drilling the hole, an end for connecting to a drill, and a middle portion between the two ends;
a sleeve surrounding at least the shaft's middle portion in a longitudinally slidable manner, at least part of an inner surface of the sleeve engaging at least part of an outer surface of the shaft's middle portion in a manner that prevents relative rotation between the sleeve and the shaft;
a countersink drill bit provided at an end of the sleeve that is proximate the shaft's drilling end; and
a locking mechanism configured to engage with the shaft's middle portion and hold the sleeve in a longitudinally fixed position with respect to the shaft, thereby locating the countersink drill bit at a selected position with respect to the shaft's drilling end;
wherein the outer surface of the shaft's middle portion comprises a series of angled ratchet grooves with which the locking mechanism is configured to engage so as to allow for incremental adjustment of the countersink drill bit with respect to the shaft's drilling end; and
wherein a given ratchet groove in the series of ratchet grooves has a first surface proximate the shaft's drilling end that is non-perpendicular with respect to a longitudinal axis of the shaft and over which the locking mechanism slides as the sleeve is moved toward the shaft's drilling end and has a second surface proximate the shaft's connecting end that is perpendicular to the longitudinal axis of the shaft such that the locking mechanism must be removed from the given ratchet groove before the sleeve can be moved toward the shaft's connecting end.

11. The instrument of claim 10, wherein the locking mechanism comprises a finger on the sleeve having an axially-inwardly facing ratchet tooth configured to be received in one of the ratchet grooves.

12. The instrument of claim 11, further comprising a release mechanism that when actuated lifts the ratchet tooth of the finger out of the ratchet groove.

13. The instrument of claim 10, wherein the locking mechanism comprises a spring-loaded wire having a locking portion that at least partially surrounds the outer surface of the shaft's middle portion and is configured to be received in one of the ratchet grooves.

14. The instrument of claim 13, wherein the wire has two legs, first ends of which are configured to be coupled to the sleeve and second ends of which are connected by the locking portion, and wherein the locking mechanism further comprises handles formed from the wire on either side of the locking portion, the locking mechanism being configured such that force applied to the handles causes the locking portion to be removed from the ratchet groove.

15. The instrument of claim 10, wherein the sleeve's inner surface is complementary to the outer surface of the shaft's middle portion.

16. The instrument of claim 15, wherein the sleeve's inner surface and the shaft's middle portion have the same cross-sectional shape.

\* \* \* \* \*

UNITED STATES PATENT AND TRADEMARK OFFICE
CERTIFICATE OF CORRECTION

| | | |
|---|---|---|
| PATENT NO. | : 11,045,212 B2 | Page 1 of 1 |
| APPLICATION NO. | : 16/357867 | |
| DATED | : June 29, 2021 | |
| INVENTOR(S) | : Douglas Pacaccio, Jeremy Blair and Emmanuel Anapliotis | |

It is certified that error appears in the above-identified patent and that said Letters Patent is hereby corrected as shown below:

On the Title Page

Item (72), delete "Douglas Pacaccio, Sycamore, FL (US)" and insert -- Douglas Pacaccio, Sycamore, IL (US) --

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*